United States Patent
Van Erlach et al.

(10) Patent No.: US 7,232,460 B2
(45) Date of Patent: Jun. 19, 2007

(54) NANODEVICES, MICRODEVICES AND SENSORS ON IN-VIVO STRUCTURES AND METHOD FOR THE SAME

(75) Inventors: Julian Van Erlach, Clifton Park, NY (US); Arlen L. Olsen, Clifton Park, NY (US); Jeffrey M. Smith, Pittsfield, MA (US); Laura B. Smith, Pittsfield, MA (US); Gerald E. Bender, Cheshire, MA (US); Audra L. Stinchcomb, Latham, NY (US); Denis P. Donnelly, Saratoga Springs, NY (US); James E. Peterson, Delmar, NY (US); Roger D. Whitmer, Pittsfield, MA (US); Gerald F. Dudding, Clifton Park, NY (US); Mark D. Scott, Clifton Park, NY (US)

(73) Assignee: Xillus, Inc., Latham, NY (US)

( * ) Notice: Subject to any disclaimer, the term of this patent is extended or adjusted under 35 U.S.C. 154(b) by 623 days.

(21) Appl. No.: 10/132,555

(22) Filed: Apr. 25, 2002

(65) Prior Publication Data

US 2003/0032892 A1   Feb. 13, 2003

Related U.S. Application Data

(60) Provisional application No. 60/286,739, filed on Apr. 25, 2001.

(51) Int. Cl.
*A61F 2/06* (2006.01)
*A61B 5/00* (2006.01)

(52) U.S. Cl. ............ 623/1.15; 600/547; 600/587

(58) Field of Classification Search ........ 600/309–310, 600/547, 587; 604/890.1; 623/1.11–1.12, 623/1.15
See application file for complete search history.

(56) References Cited

U.S. PATENT DOCUMENTS

| | | | | |
|---|---|---|---|---|
| 5,250,439 A | * | 10/1993 | Musho et al. | 205/778 |
| 5,328,471 A | * | 7/1994 | Slepian | 604/101.03 |
| 5,840,008 A | * | 11/1998 | Klein et al. | 600/7 |
| 5,879,329 A | * | 3/1999 | Ginsburg | 604/98.01 |
| 5,906,640 A | * | 5/1999 | Penn et al. | 623/1.15 |
| 5,967,986 A | * | 10/1999 | Cimochowski et al. | 600/454 |
| 6,152,869 A | * | 11/2000 | Park et al. | 600/3 |
| 6,358,247 B1 | | 3/2001 | Altman et al. | |
| 6,214,040 B1 | * | 4/2001 | Jayaraman | 623/1.13 |
| 6,231,516 B1 | * | 5/2001 | Keilman et al. | 600/485 |

(Continued)

OTHER PUBLICATIONS

Webster's II New Riverside University Dictionary, Riverside Publishing Company, 1994, p. 71.*
Chemical and Engineering News, "Tying Top-Down to Bottom-Up" M. Freemantle, pp. 27-29, Feb. 5, 2001.
Chemical and Engineering News, "Promising Lead for Molecular Wires", Christopher E.D. Chidsey et al, p. 37, Feb. 26, 2001.
Chemical and Engineering News, "Polymer Nanowires Connected by STM", Y. Okawa et al., pp. 38, Mar. 5, 2001.

(Continued)

*Primary Examiner*—Eric F. Winakur
(74) *Attorney, Agent, or Firm*—Schmeiser, Olsen & Watts

(57) ABSTRACT

An in-vivo method and apparatus is disclosed that comprises at least one sensor for determining changes in a human's an animal's body and reporting said changes outside the body. The sensor may be embedded in a sheath. The apparatus may be used to monitor chemical or physical changes in the body fluids. Alternatively, the apparatus may be used to monitor and regulate chemical or physical levels in humans and animals.

1 Claim, 14 Drawing Sheets

U.S. PATENT DOCUMENTS 6,383,171 B1 * 5/2002 Gifford et al. ............... 604/508
6,442,413 B1 * 8/2002 Silver .......................... 600/347
6,447,439 B1 * 9/2002 Vallana et al. .................. 600/3
6,669,683 B2 * 12/2003 Santini et al. ............ 604/890.1
2002/0183686 A1 * 12/2002 Darvish et al. ................ 604/21

OTHER PUBLICATIONS

Alt Healthwatch, Townsend letter for doctors and patients, Jun. 1995, "Fungal/Mycotoxin Conference: Excerpts From Dr. Wood's Presentation, Sep. 30, 1994-Oct. 2, 1994", pp. 143, 9-10 (1995).

* cited by examiner

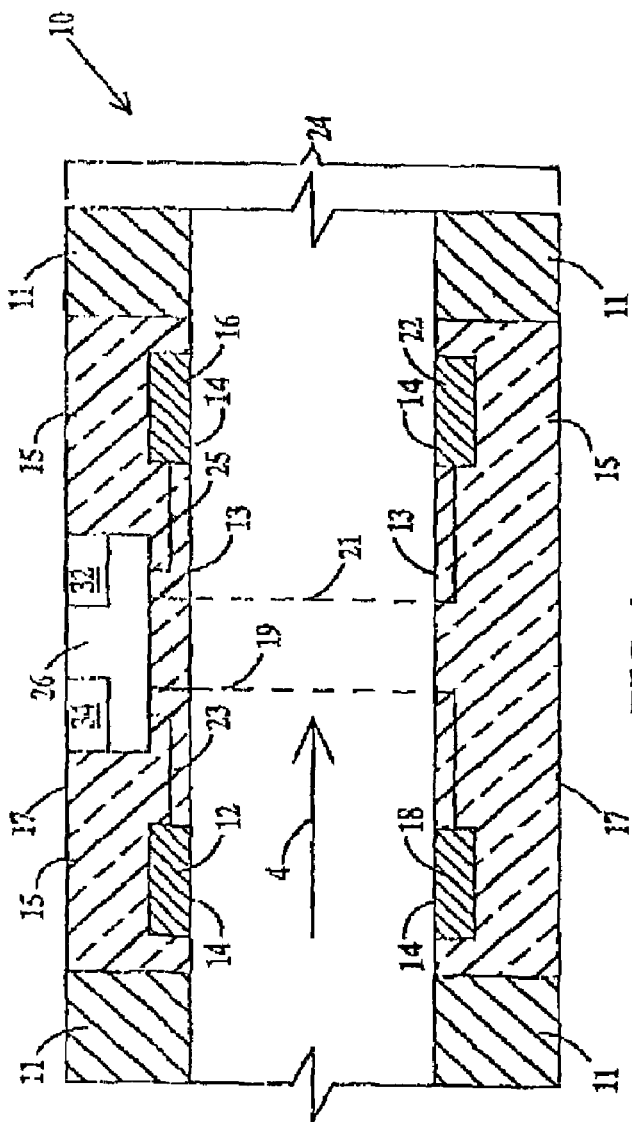
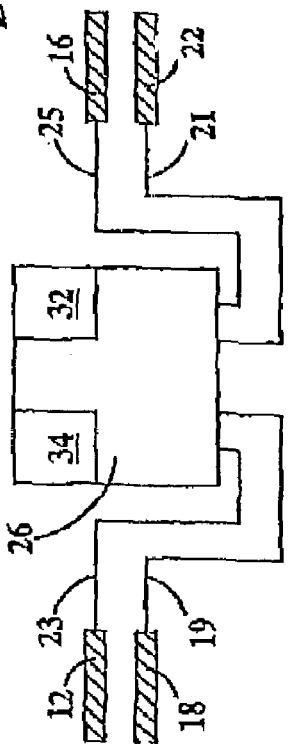
FIG. 1
FIG. 2

NANODEVICES, MICRODEVICES AND SENSORS ON IN-VIVO STRUCTURES AND METHOD FOR THE SAME

This application claims the benefit of priority under 35 U.S.C. §119(e) to U.S. Provisional Patent Application No. 60/286,739, filed Apr. 25, 2001.

BACKGROUND OF THE INVENTION

1. Technical Field

This invention relates to a method and apparatus for forming devices on substrates and using these devices to provide in-vivo treatment of certain disease conditions in animals and humans. Specifically, the present invention relates to a method and apparatus for nanodevices, microdevices, and sensors on in-vivo structures.

2. Background Art

Typically diagnosis of animal and human diseases or body disfunctions involves testing a person's physical parameters such as blood pressure, temperature and pulse. Additionally, diagnosis commonly requires removing samples of blood and other body fluids and subjecting them to diagnostic tests to determine levels of enzymes, metabolites, toxins or other chemicals essential to life. Medical imaging instruments based on inter alia x-ray, ultrasound or magnetic resonance provide additional information used by the medical profession to diagnose causes of animal and human illness. Once diagnosed, the ailment may commonly be treated inter alia using drugs administered transdermally, orally or by injection.

Diagnosis and treatment by these common techniques may be difficult because physical and chemical testing is not sufficiently specific to the diseased or disfunctional part of the body. Also, drug effectiveness may be reduced because traditional methods of introduction are not specifically directed to the diseased or disfunctional part of the body.

SUMMARY OF THE INVENTION

The present invention overcomes the deficiencies of the related art by providing an apparatus comprising nanodevices, microdevices and sensors on in-vivo structures and method for the same. Also disclosed is a device that is insertable into a body passage or implantable into body tissue, wherein a sensor operatively attached to a device determines changes in body conditions, and wherein the apparatus reports the changes. The biosensors transmit wirelessly outside or within the body.

BRIEF DESCRIPTION OF THE DRAWINGS

These and other features and advantages of this invention will be more readily understood from the following detailed description of the various aspects of the invention taken in conjunction with the accompanying drawings in which:

FIG. 1 depicts a longitudinal cross-section of an apparatus of the present invention;

FIG. 2 depicts an expandable longitudinal cross section of a structure of an embodiment of the present invention;

DETAILED DESCRIPTION OF THE INVENTION

Figure 3:
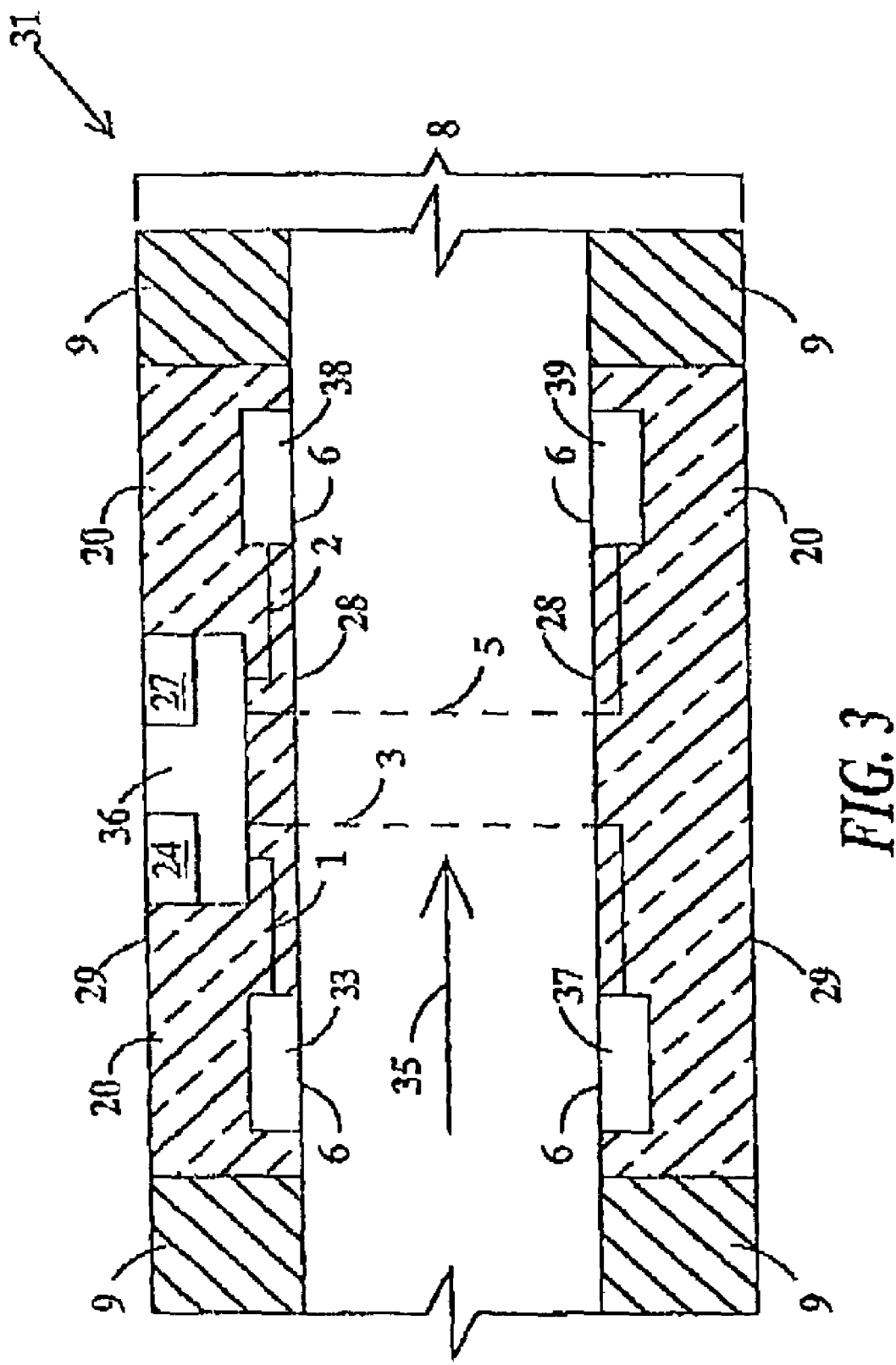
FIG. 3 depicts a longitudinal cross-section of an apparatus, comprising light emitting devices and light sensing detectors operatively attached to an inner surface of a tube.

FIG. 1 depicts a longitudinal cross-section of an in-vivo apparatus 10 that comprises a tube 24 having an inner surface 13, an outer surface 17 and a body 11. Hereinafter, a "tube" is a portion of an "internal medical device" such as a catheter, stent, endoscope, defibrillator or the like. The catheter, endoscope, or defibrillator may be used for biodetection of infection or patient monitoring, e.g., liver, heart enzymes and blood glucose. Hereinafter, a "stent" is a small, expandable wire mesh tube. The stent may be either a vascular stent or a urinary stent. The defibrillator is an implantable defibrillator such as that disclosed in U.S. Pat. No. 6,358,247 which is hereby incorporated by reference. "Nanodevice(s)" may be any inorganic device on the order of magnitude of 1 nanometer (nm) to 800 nanometers. However, a typical nanodevice will be between 5–100 nm. Examples of nanodevices include nanotubes, nanoparticles (such as lithium particles), buckyballs, and nanowires made from silicon, gallium nitride, zinc oxide and other semiconducting inorganic materials such as oxides of transition metals or semiconducting organic materials.

The body 11 further comprises conductive contacts 12, 16, 18, and 22 operatively attached to and coplanar 14 with the inner surface 13 of the tube 24. Referring to FIG. 1, contact 12 may be oriented opposite and parallel to contact 18, and contact 16 may be oriented opposite and parallel to contact 22. Alternatively, contact 12 may be oriented opposite and parallel to contact 18, and contacts 16 may be oriented orthogonal to contact 22. The body 11 of the tube 24 may be made from electrically insulating materials such as polyethylene, polypropylene, silicone elastomer, nylon, or polytetrafluoroethylene. The tube 24 may also be made from nitinol[7], a typical nickel/tin metal alloy. The apparatus 10 further may include a microchip 26 that is electrically coupled to conductor 23 and to conductive contact 12 and additionally to conductor 25 and to conductive contact 16. The microchip 26 further comprises an on-chip battery 32 or like source of electromotive force (EMF). The microchip is capable of passive remote EM interrogation. In addition the microchip 26 may further comprise a receiver/transmitter device 34. The receiver/transmitter 34 may include an FM receiver having a receiving/transmitting antenna. Microchip 26 is conductively coupled to the receiving/transmitting antenna. When the body 11 of the tube 24 is made from electrical conductors such as metal or metal alloys such as nitinol[7], the conductive components of apparatus 11 must be electrically insulated to prevent malfunction due to shorting. The microchip 26, the conductors, 23, 25, 19, and 21 and conductive contacts 12, 16, 18, and 22 are encapsulated by insulator 15. The insulator 15 may be made from silica, silicone elastomer, insulating plastics such as Ultem™ from General Electric Co., nylon, acrylic, polypropylene, polyethylene or polytetrafluoroethylene or similar electrically insulating material.

FIG. 2 defines a structure 30 comprising two circuits controlled by the microchip 36. In one circuit comprising the microchip 26, conductors 23 and 19, the microchip 26 determines a resistance (R1) between the contacts 12 and 18 using Ohm's Law (see formula 1 infra). In a second circuit comprising the microchip 26, conductors 25 and 21, the microchip 26 determines a resistance (R2) between the contact 16 and 22. R1 and R2 from the microchip 26 are transmitted through the animal's or human's skin using the transmitter/receiver 34. Voltage and current values may be transmitted to the microchip 26 using the transmitter/receiver 34. When the body 11 of the tube 24 is made from metal or metal alloy such as nitinol, the inner surface 13 and the outer surface 17 of the tube 24 may be electrically insulated by coating or sheathing (as described in FIGS. 11–13) with silica, silicone elastomer, insulating plastics such as Ultem™ from General Electric Co., nylon, acrylic, polypropylene, polyethylene or polytetrafluoroethylene or similar electrically insulating material to avoid interfering with the determination of R1 and R2.

$$R=V/I. \quad (1)$$

(where R=resistance, V=voltage and I=current)

The circuits and field effect transistor (FET) devices in microchip 26 of FIG. 2 may be formed according to a method of Dr. G. Julius Vansco et al., who demonstrated that self-assembled thin films of organic-organometallic diblock copolymers made up of poly(isoprene) and poly(ferrocenyldimethylsilane)(PFS) are promising candidates for nanolithography. ("Tying Top-Down to bottom Up," *Chemical and Engineering News*, 27, 28, Feb. 5, 2001. Hereinafter "nanolithography" is a form of lithography that provides resolution for forming electronic structures that have a maximum dimension equal to or greater than about 5 to 10 nanometers. Polymer chemistry can be used to produce nanometer-sized patterns on silicon wafers using one-step lithographic reactive-ion etching procedures. One key enabling tool for nanotechnology includes scanning probe techniques such as electrochemical atomic force microscopy. Another key tool to enable forming devices such as micro-chip 26 is chemical self-assembly. Hereinafter, "chemical self-assembly" is the self-organization of small molecular components to form complex functional structures." Hereinafter, "nanotechnology" is the study of forming miniaturized electronic devices that include devices that have a maximum dimension equal to or greater than about 5 to 10 μm.

Conductors 23, 25 19 and 21 illustrated in FIG. 1 may be formed according to a method of Christopher E. D. Chidsey et al., who demonstrated electron tunneling through oligophenylenevinylene (OPV) conductors having ferrocene at one end and thiol at the other "is so fast they could make good molecular wires." Christopher E. D. Chidsey et al., "Promising Lead for Molecular Wires, *Chemical and Engineering News*, 37, Feb. 26, 2001. Using OPV units from about 0.1 to 28 Angstroms (Å) (from about 0.003 to 0.28 μm) having a ferrocene at one end and a gold electrode at the other, John F. Smalley et al. demonstrated no drop in a rate of electron transfer. Id. at 37.

Alternatively, conductors 23, 25 19 and 21 illustrated in FIG. 1 may be formed according to a method of Yuji Okawa et al. who used a scanning tunneling microscope (STM) to form electrically conductive polymer nanowires from 10,12-nonacosadiynoic acid shown in formula (2) infra. Y. Okawa et al., "Polymer Nanowires Connected by STM," *Chemical and Engineering*

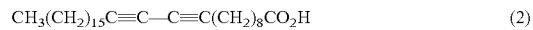

$$CH_3(CH_2)_{15}C\equiv C-C\equiv C(CH_2)_8CO_2H \quad (2)$$

*News*, 38, 38, Mar. 5, 2001. Hereinafter, "polymer nanowire" is a linear polymer chain having a length ranging from about 3 to 300 nm (from about 0.003 to 0.3 μm). Id. at 38. Okawa et al. reported ". . . demonstrating that we can initiate linearly propagating chain polymerization of organic molecules at any predetermined point and terminate it at another predetermined point with a spatial precision on the order of 1 nm. (0.001 μm)." Id.

In an embodiment of the present invention, referring to FIG. 1, the apparatus 10 comprises a tube 24 that may be inserted into a body passage that includes body passages that have a maximum diameter greater than or equal to about 5 to 10 μm. Lubricating the outer surface 17 of the tube 24 with materials such as petroleum jelly or mineral oil or compressing the tube 24 adapts the tube 24 for insertion. FIG. 1 illustrates that the body fluid in the vessel travels through the apparatus 10 in a direction depicted by arrow 4. Hereinafter, a "vessel" is any artery, vein, capillary, duct or channel or the like in an animal or human body that carries body fluids. The microchip 26 supplies sufficient EMF to the circuit comprising contacts 12 and 18 and to the circuit comprising contacts 16 and 22 to obtain a resistance in the range of about 50 to 310 ohms when the body fluid flows through the tube 24 in the direction of the arrow 4. The microchip 26 transmits a value of R1 and R2. Monitoring the values over time is used to indicate an onset of disease in the animal or human body.

In June, 1995, remarks of Dr. Alexander Wood were reported in which he stated a use of measurement of resistance of blood in humans. Dr. Wood reported "the ideal resistance of venous blood should be between 180 to 210 ohms." See "Fungal/Mycotoxin Conference: Excerpts From Dr. Wood's Presentation; Sept. 30 to Oct. 2, 1994," *Alt Healthwatch*, 143, 9–10 (1995). Dr. Wood further reported ". . . 1) [h]igh resistivity level, between 210 and 300 Ohms, indicates that there are not enough trace elements needed by the enymes to digest food; 2) low resistivity level, dropping below 180 Ohms, indicates that the organs, such as the liver and the pancreas are beginning to show stress. Low resistivity also indicates the presence of a toxic load in the digestive system." See Id., supra. Dr. Wood also reported "the ideal resistivity of saliva is about the same as for blood." See Id., supra. In addition, according to Dr. Wood, "the ideal resistivity of urine is 30 Ohms. . . . The resistivity of the urine will rise dramatically to between 60 and 120 Ohms, a clear indication that the body's ability to eliminate waste is being compromised." See Id., supra.

Referring to FIG. 1, when the tube 24 in an internal medical device or an apparatus 10 is a stent, the apparatus 10 may function as a typical stent in a post-angioplasty medical procedure. Throughout the specification, where a stent is referred to it is also understood that the stent may be any internal medical device as hereinbefore defined. With respect to a stent, it was first performed in the mid-1980s, and first approved by the FDA in the mid-1990s, stenting is a catheter-based procedure in which a stent (a small, expandable wire mesh tube) is inserted into a diseased artery to hold it open. Although stenting reduces a risk of a newly opened artery re-closing (restenosis), there is a need to monitor for restenosis. Hereinafter, "restenosis" is a proliferation of cell growth that causes inter alia varying degree of re-closing of the artery. The microchip 26 includes software that controls the function of the microchip 26 that includes accessing calibration files for correlating resistance to restenosis. The software on microchip 26 further controls transmitting R1 and R2 through the animal's or human's skin using the receiver/transmitter 34. Since resistivity varies directly as a function of a diameter of the artery, comparison of a value of R1 and R2 over time indicates if a portion of the stent 24 has narrowed over time. Substantially similar reduction in the value of R1 and R2 over time anticipates collapse of the stent 24.

Referring to FIG. 1, collapse of the stent 24 may cause a disease condition. Use of the alternative embodiment of apparatus 10, described supra, wherein contact 12 may be oriented opposite and parallel to contact 18, and contact 16 may be oriented orthogonal to contact 22 enables distinguishing between collapse of the stent 24 and restenosis. Biosensors would detect the vascular diameter and arrive at a given resistance for a given diameter. As diameter in the stent changes, so would the resistance. In the case of collapse of the stent 24, resistance would remain constant across contacts orthogonal to one another, but resistance would decrease across opposite and parallel contacts. The change in diameter may be determined by either one pair of biosensors or a plurality of biosensors.

Figure 10:
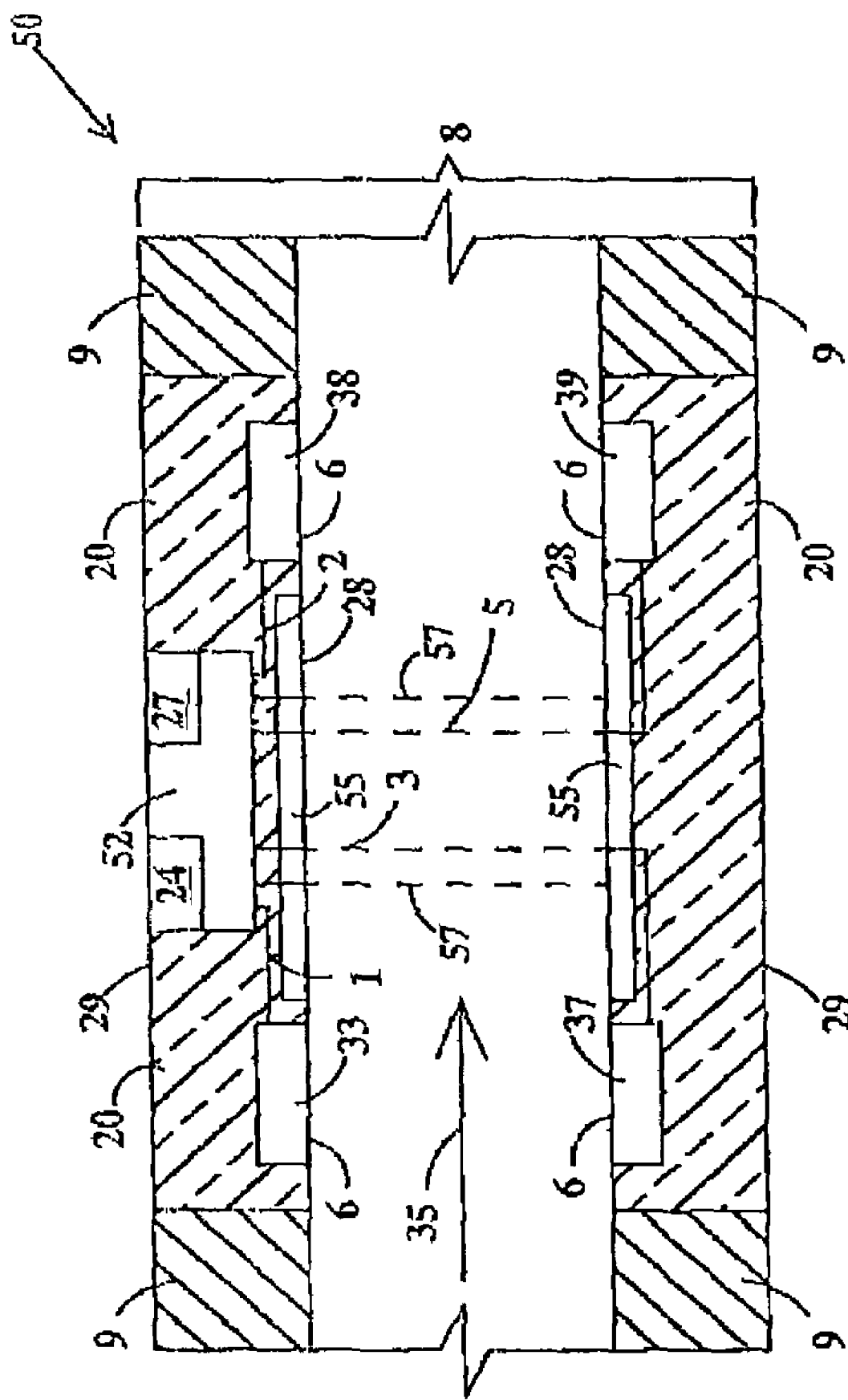
FIG. 10 depicts FIG. 3, further comprising a means for delivering a disease treatment agent through a wall of the tube.

In addition to the embodiment of the present invention using the apparatus 10 to monitor R1 and R2 in the animal's or human's body fluids, an alternative embodiment of the present invention is apparatus 10 further comprising a drug delivery system depicted in FIG. 10 and described in associated text infra, to monitor and deliver a disease treatment agent such as rapamycin into the animal's or human's body fluid to retard or halt restenosis. Referring to FIG. 1, more than one apparatus 10 further comprising the drug delivery system depicted in FIG. 10 infra may be used to detect restenosis or other disease condition resulting in change in the resistance between conductive contacts 12 and 18 or 16 and 22. The microchip 26 of apparatus 10 includes software to network in-vivo between the stents. Hereinafter, "network" is a cross-functional communication between microchips to monitor R1 and R2 and provide a coordinated delivery of disease treatment agent.

In another embodiment of the present invention, FIG. 3 depicts a longitudinal cross-section of an in-vivo apparatus 31, comprising a tube 8, that may be inserted into a body passage cavity or attached to an organ that includes vessels. The tube 8 may be adapted for insertion into the body vessel as described supra for FIG. 1 and associated text. FIG. 3 illustrates that the body fluid in the vessel travels through the apparatus 31 in a direction depicted by arrow 35. The tube 8 that includes catheters and stents further comprises an inner surface 28, an outer surface 29 and a body 9. The body 9 further comprises light emitting diodes or lasers 33, and 38 and light sensors 37 and a 39 operatively attached to and coplanar 6 with the inner surface 28 of the tube 8. Referring to FIG. 3, light emitting diode or laser 38 may be oriented opposite and parallel to light sensor 39, and light emitting diode or laser 33 may be oriented opposite and parallel to light sensor 37. Alternatively, light emitting diode or laser 33 and light sensor 37 may be oriented in a non-opposite and non-parallel orientation to optimize a signal to noise ratio (S/N). Hereinafter, a "signal" is a response from a sensor due to absorption, transmission or fluorescence of light from a light emitting diode or laser by a chemical analyte or by a solid state photoreceptor such as that developed by Foveon, Inc. Hereinafter, "noise" is a response from sensor due to response of a sensor to light scattering of the light from a light emitting diode or laser. A test that a signal is real instead of noise is that the signal to noise ratio (S/N) is greater than 2.0. Hereinafter, a "chemical analyte" is an enzyme, metabolite, toxin or chemical essential to life. The body 9 of the tube 8 may be made from electrically insulating materials such as polyethylene, polypropylene, silicone elastomer, nylon, or polytetrafluoroethylene. The tube 8 may also be made from nitinol[7], a typical nickeltin metal alloy. The apparatus 31 further comprises a microchip 36 that is electrically coupled to conductor 1 and to light emitting diode or laser 33 and additionally to conductor 2 and to light emitting diode or laser 38. In addition, the microchip 36 may be electrically coupled to conductor 3 and light sensor 37 and additionally to conductor 5 and light sensor 39. The microchip 36 may further comprise an on-chip battery 24 or like source of electromotive force (EMF). In addition the microchip 36 may further include a receiver/transmitter device 27. The microchip 36, the conductors, 1, 2, 3 and 5 and light emitting diodes or lasers 33, and 38 and light sensors 37 and 39 are encapsulated by electrical insulator 15 when the body 9 of the tube 8 is made from electrical conductors such as metal or metal alloys such as nitinol to prevent malfunction due to shorting. The insulator 15 may be made from silica, silicone elastomer, insulating plastics such as Ultem™ from General Electric Co., nylon, acrylic, polypropylene, polyethylene or polytetrafluoroethylene or similar electrically insulating material.

Referring to FIG. 3, when the tube 8 in apparatus 31 is a stent, the apparatus 31 may function as a typical stent in a post-angioplasty medical procedure. As described supra for FIG. 1 and associated text, there is a need to monitor the stent 8 for restenosis. Formula 3 depicts an inverse square law relating light energy, luminescence (intensity) and distance between the source of the light, such as light emitting diodes 33 or 38 and a sensor of the light, such as a light sensors 37 or 39.

$$\text{Light Energy} = \text{Intensity}/\text{distance}^2 \tag{3}$$

If X is the energy detected by a sensor of light when the source and the sensor are separated by 1 meter, 0.25×will be the energy detected by the sensor of light when the same source and sensor are separated by 2 meters. Light sensors 37 and 39 respond to a light energy from light emitting diodes or lasers 33 and 38 over time and the response from light sensor 37 is electrically conducted to microchip 36 through conductor 3 and the response from light sensor 39 is electrically conducted to microchip 36 through conductor 5 over time. Hereinafter, the combined circuit comprising the light sensors 37 and 39, light emitting diodes 33 and 38, the microchip 36 and associated conductors 1, 2, 3 and 5 comprises a "monitoring circuit". Microchip 36 determines the light energy change over time using formula (3), and transmits the light energy change from light sensors 37 and 39 outside the animal's or human's body using the receiver/transmitter 27. Monitoring the light energy from light sensors 37 and 39 over time is used to test for vascular patency in the animal or human body. Hereinafter, "vascular patency" is the state of an artery or vessel being open. Occlusion of the vessel by either collapse or blockage (e.g., clot formation) will alter light transmittance. Characteristics of light transmittance is a function of Diameter of the stent and the presence of serum and vascular cells (erythrocytes, leukocytes, and platelets).

Figure 4:
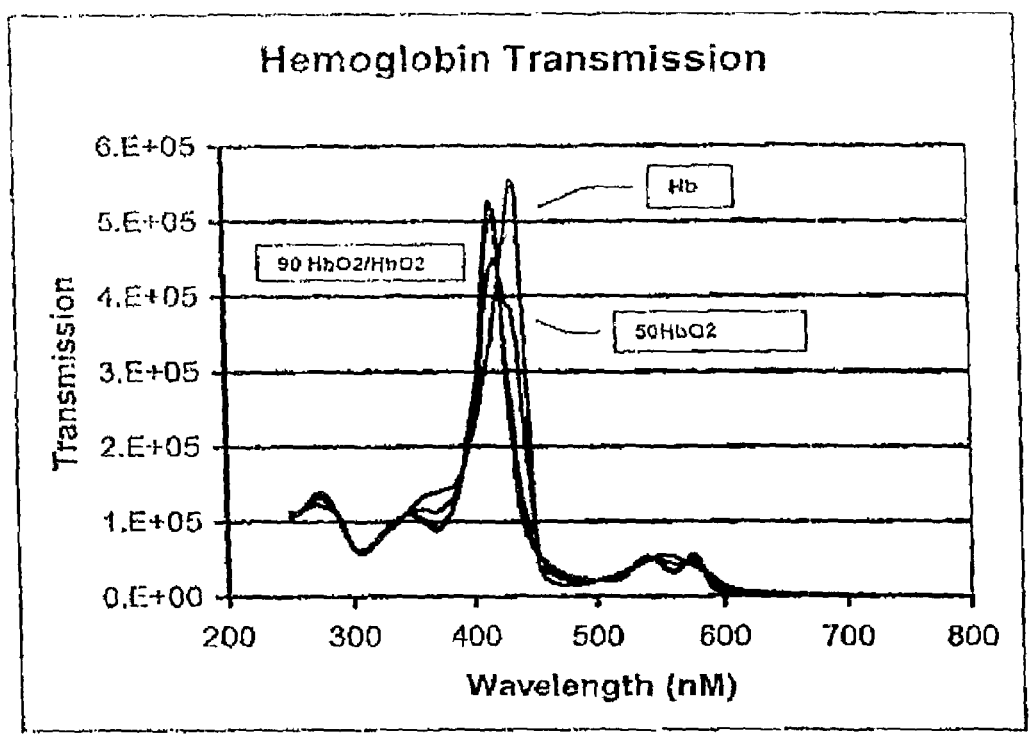
FIG. 4 depicts a hemoglobin transmission spectrum, wherein an oxygen content of the hemoglobin ranges from 0–100%.
Figure 5:
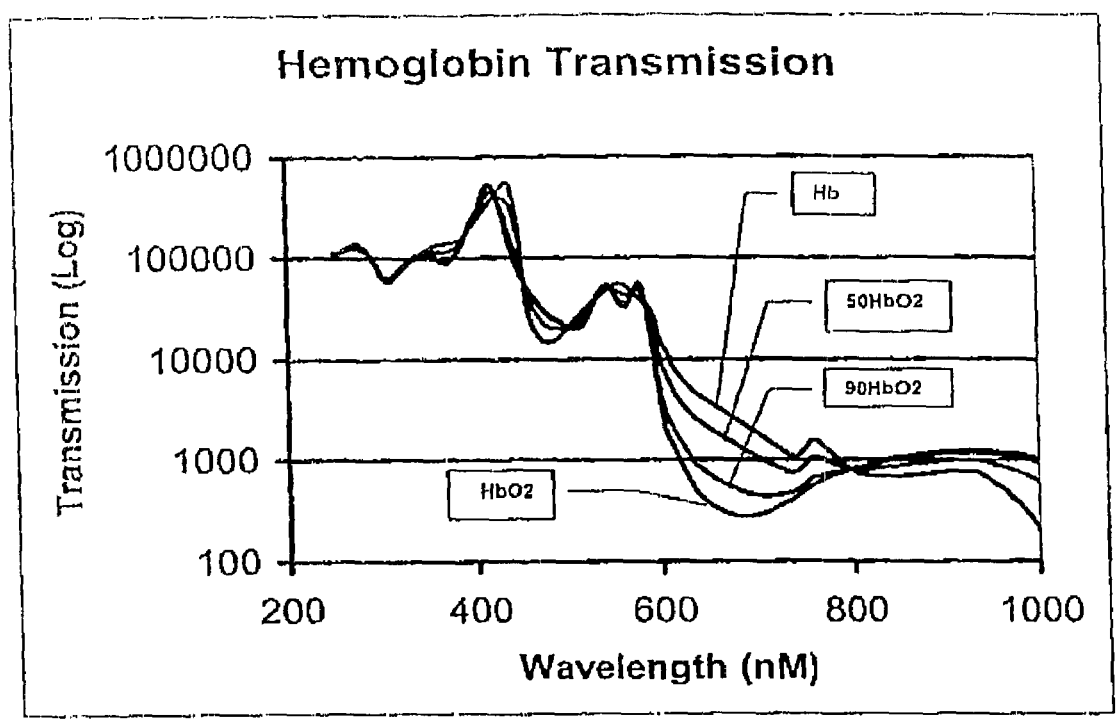
FIG. 5 depicts a hemoglobin transmission (Log) spectrum, wherein an oxygen content of the hemoglobin ranges from 0–100%.

In an alternative embodiment, FIG. 4 depicts a transmission spectrum for hemoglobin having no oxygen, 50% oxygenated hemoglobin, 90% oxygenated hemoglobin and 100% oxygenaged hemoglobin. FIG. 5 depicts a hemoglobin transmission (Log) spectrum illustrating that the greatest variability in spectra from hemoglobin having the aforementioned levels of oxygen is in a range between about 600 nm and 800 nm.

Figure 6:
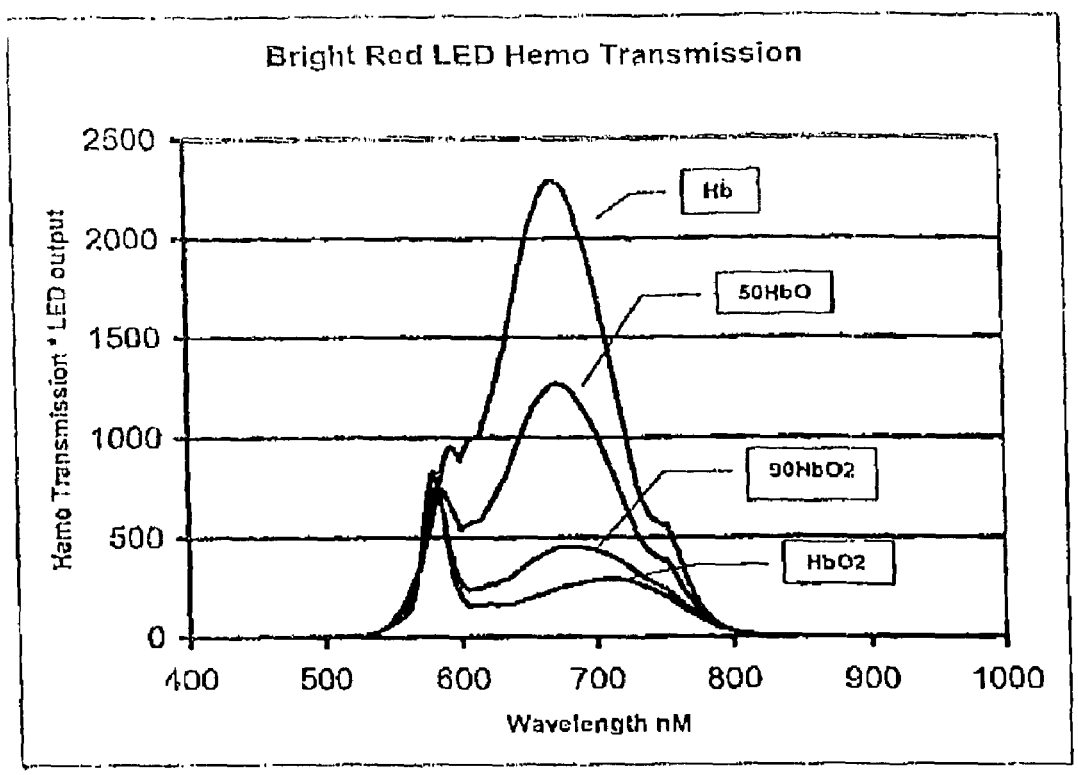
FIG. 6 depicts a bright red light emitting diode transmission of hemoglobin, wherein an oxygen content of the hemoglobin ranges from 0–100%.
Figure 7:
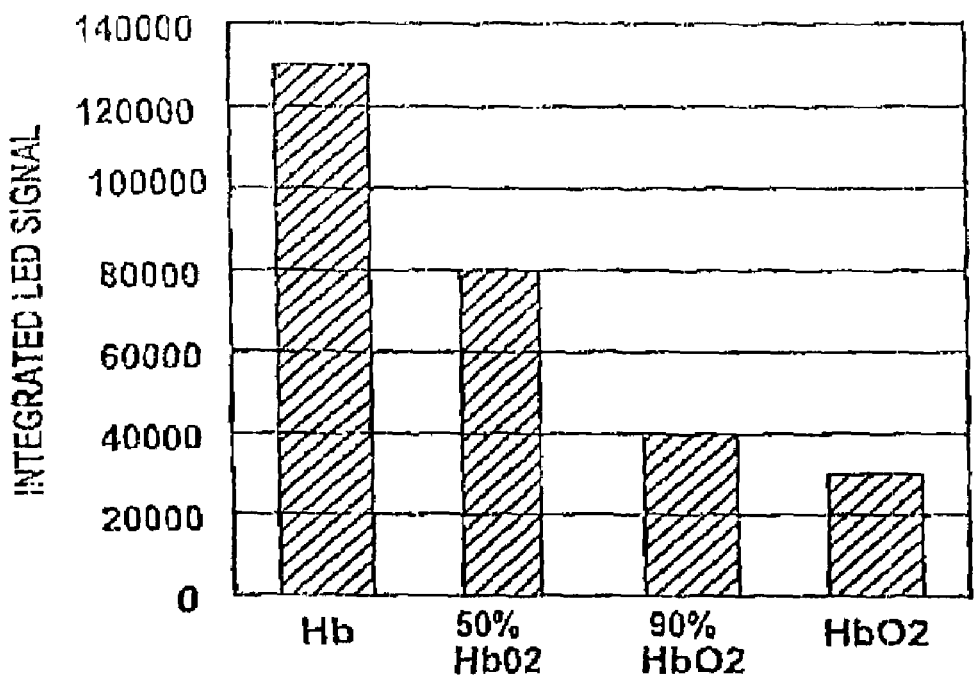
FIG. 7 depicts an integrated bright red light emitting diode transmission through hemoglobin, wherein an oxygen content of the hemoglobin ranges from 0–100%.

FIG. 6 depicts a transmission of bright red light emitting diode through hemoglobin having no oxygen, 50% oxygenated hemoglobin, 90% oxygenated hemoglobin and 100% oxygenaged hemoglobin. A single photodiode would see the total integrated power of the product of the diode response and the hemoglobin transmission. The integrated power would be highest for the non-oxygenated blood and lowest for the 100% oxygenated hemoglobin. FIG. 7 depicts an integrated bright red light emitting diode and hemoglobin transmission through hemoglobin having no oxygen, 50% oxygenated hemoglobin, 90% oxygenated hemoglobin and 100% oxygenated hemoglobin.

Figure 8:
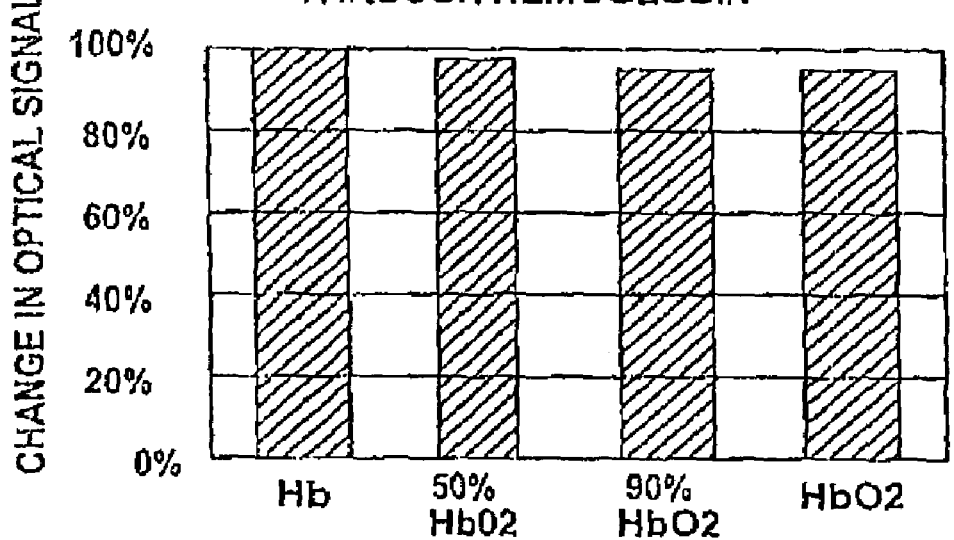
FIG. 8 depicts a percent change of an integrated bright green light emitting diode transmission through hemoglobin, wherein an oxygen content of the hemoglobin ranges from 0–100%.
Figure 9:
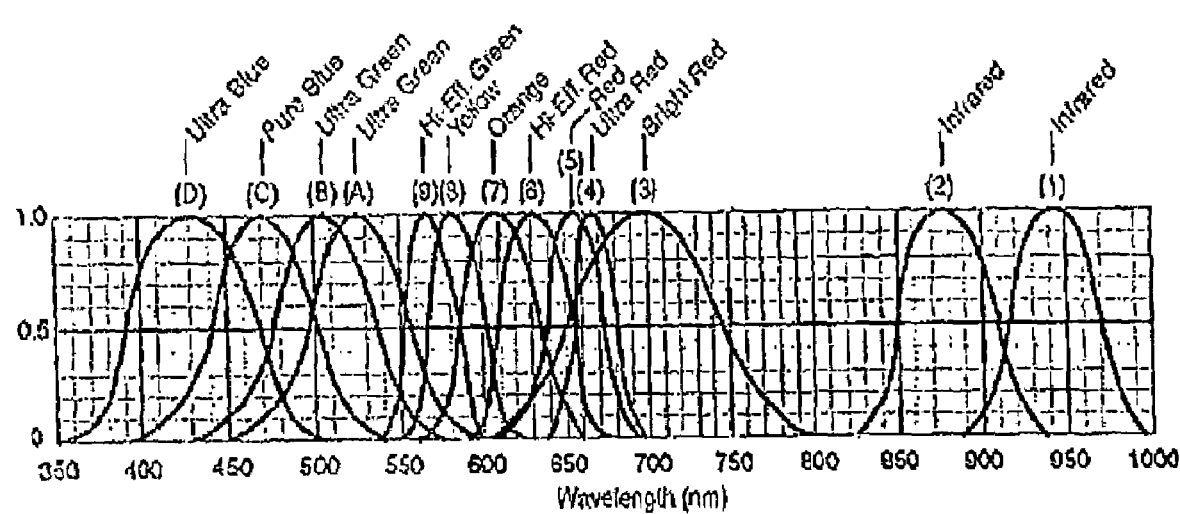
FIG. 9 depicts a range of wavelengths and intensities for light emitting diodes.

FIG. 8 depicts a transmission of bright green light emitting diode through hemoglobin having no oxygen, 50% oxygenated hemoglobin, 90% oxygenated hemoglobin and 100% oxygenated hemoglobin. The transmission of the bright green light emitting diode was insensitive to the oxygen percentage, since the transmission only diminished from 0–10% in the range from about non-oxygenated hemoglobin to 100% oxygenated hemoglobin. Since the bright green light emitting diode transmission was insensitive to the hemoglobin oxygen percentage, the bright green light emitting diode could act a reference that would correct for overall transmission changes due to physical light path length changes and fluid density changes. FIG. 9 depicts a range of transmission wavelengths for light emitting diodes. As depicted in FIG. 5 and described in associated text, a single bright red light emitting diode would see the total integrated power of the product of the diode response and the hemoglobin transmission.

Referring to FIG. 3, microchip 36 is used to process a response from the light sensor 37 from transmission using bright red light emitting diode 33 through hemoglobin, wherein the processing produces a signal, S1, that is transmitted through the animal's or human's skin. Microchip 36 is further used to process a response from the light sensor 39 from transmission using bright green light emitting diode 38 through hemoglobin, wherein the processing produces a signal, S2, that is also transmitted through the animal's or human's skin using receiver/transmitter 27. Subtraction of S2 from S1 using commercially available computer software yields a corrected transmission signal, wherein the corrected transmission signal is proportional to a correct oxygenation level of the hemoglobin flowing through the apparatus 35.

Another embodiment of the present invention is depicted in FIG. 10, comprising the apparatus 50 that may include delivering a disease treatment agent into the animal's or human's body fluid and monitoring for a disease condition. FIG. 10 depicts FIG. 3, further comprising: a disease treatment agent reservoir 55 that is oriented coplanar 6 with the inner surface 28 of the tube 8; a microchip 52 operatively coupled to a drug delivery circuit 57 that controls a rate of delivery of a disease treatment agent from the disease treatment agent reservoir 55 to the animal's or human's body fluid. The microchip 52 is also operatively coupled to the monitoring circuit depicted in FIG. 3 supra and described in associated text.

Referring to FIG. 10, the animal's or human's body fluid flows through the apparatus 50 in a direction depicted by arrow 35. If the tube 8 is a stent, thrombolytics such as those listed in Table 1 infra may be delivered by the apparatus 50 as the disease treatment agent. The disease treatment reservoir may be made from electroresponsive polymers such as poly(dimethylaminopropylacrylamide (PDMAPAA) poly (methacrylic acid), poly(acrylic acid), alginic acid get, poly (allylamine) or from magnetically enhanced drug release polymer such as ethylene vinyl acetate copolymer (EVAc). Hereinafter, "electroresponsive polymers" are polymers which become permeable to disease treatment agents when electric current is passed through. Hereinafter, "magnetically enhanced drug release polymers" are polymers which become permeable to disease treatment agents when subjected to a magnetic field. The reservoir 55 may be comprised of a plurality of smaller, individually addressable reservoirs, each containing a minimum desired dose.

Referring to FIG. 10, more than one apparatus 50 may be used to detect a disease condition detected by monitoring chemical analytes in the animal's or human's body fluids. The microchip 52 of apparatus 50 includes software to network in-vivo between the stents. Hereinafter, "network" is a cross-functional communication between microchips to monitor R1 and R2 and provide a coordinated delivery of disease treatment agent. Alternatively, the networking between microchips 52 in 2 or more stents 8 in the animal's or human's body fluid may be controlled by software located in a computer or other data processing device outside the body.

Referring to FIG. 10, the apparatus 50 may include one or more enzyme, sound, pressure pulse, pH and viral, bacterial or biochemical or other biochemical sensors to detect a disease condition. Hereinafter "disease condition" is preheart failure condition or abnormal heart beating through pressure/pulse detection and comparison to history. When the sensor detects sound, the determination of the disease condition may involve the Doppler effect. Hereinafter, "biochemical sensor" is a detector of a chemical substance or a vital process occurring in living organisms.

Disease treatment agents of the present invention, a dosage and a standard reconstitution volume required are listed in Table 1 infra.

TABLE 1

| Disease Treatment Agent | Dose | Standard Reconstitution Volume |
|---|---|---|
| Streptokinase (SK) (Kabikinase, Pharmacia) (Streptase, Astra) Inexpensive, 5% patients allergic reaction | 1,500,000 IU/60 min IV intercoronary: 20,000 IU bolus + 120,000/60 min | 5 ml |
| Alteplase (tPA) (Activase, Genentech) 10X SK cost, 580,000 IU/mg | 15 mg bolus 0.75 mg/kg/30 min (≦50 mg) 0.5 mg/Kg/60 min (≦35 mg | 100 mg ~100 ml |
| Reteplase (rPA) (Retavase, Boehringer Mannheim) 10 U/17.4 mg | 10 unit bolus 10 unit bolus 30 min later | 2 ml |

TABLE 1-continued

| Disease Treatment Agent | Dose | Standard Reconstitution Volume |
|---|---|---|
| Anistreplase (Eminase, SmithKline Beecham) 5% patients allergic reaction | 30 units IV over 2–5 min | |
| Tenecteplase (TNKase, Genentech) 200 U/mg | 30–50 mg IV over 5 sec | 6–10 ml |

Referring to FIG. 10, when the tube 8 in apparatus 31 is a stent, the apparatus 50 may function to monitor for restenosis in a post-angioplasty medical procedure and to deliver a thrombolytic and thrombolytic dose that includes the thrombolytics listed in Table 1 supra.

The devices of FIGS. 1–3 and 10 may include a polymer coat for embedded circuitry, RF transmission device and pharamaceutical micro or nanotubes. The pharmaceuticals may be embedded in a nanodevice such as nanotubes, nanoparticles or buckyballs. The nanodevices may be in a reservoir, in the stent or stent sheath. The luminal face of the stent will release the pharmaceutical by an induced signal via changes in a vascular occlusive event. One technique would be a current induced by changes in biopolymer permeability or gold.

Figure 11:
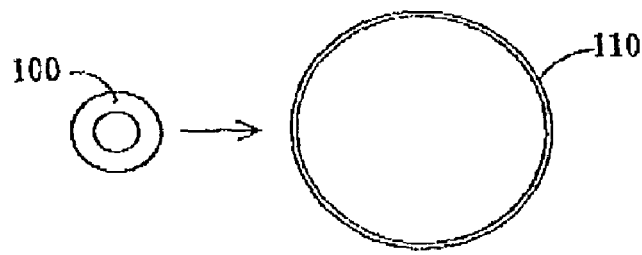
FIG. 11 depicts a cross-section of a sheath of the present invention.

Referring to FIG. 11, an elastic/stretchable sheath 100, 110 is disclosed containing flexible circuitry embedded within the sheath. The sheath is made from a biocompatible material such as Gortex® (a waterproof breathable material), polytetrafluoroethylene, stainless steel, carbon structure (e.g., carbon nanotube/nanostructure), or other material as disclosed herein for sheath materials. The sheath is depicted prior to expansion 100 and after expansion 110. Prior to expansion 100, a balloon catheter is used to insert the sheath into the body. The sheath diameter is maintained by a rigid structure such as a stent (e.g. stainless steel mesh stent), catheter, or endoscope. The balloon catheter and rigid structure are used to expand the sheath into position.

Figure 12:
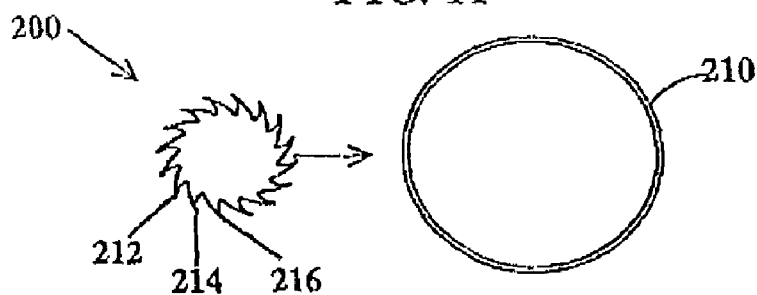
FIG. 12 depicts a cross-section of an expandable sheath of the present invention.

FIG. 12 depicts a flexible/expandable stent sheath 200, 210 containing multiple predetermined expansion sites 212, 214, 216. The circumference of the sheathing contains a plurality of predetermined sites. The sheath is made from a biocompatible material such as Gortex® (a waterproof breathable material), polytetrafluoroethylene, stainless steel, carbon structure (e.g., carbon nanotube/nanostructure), or other material as disclosed herein for sheath materials. Prior to expansion 200, a balloon catheter is used to insert the sheath into the body. The balloon catheter expands the sheath 210.

Figure 13:
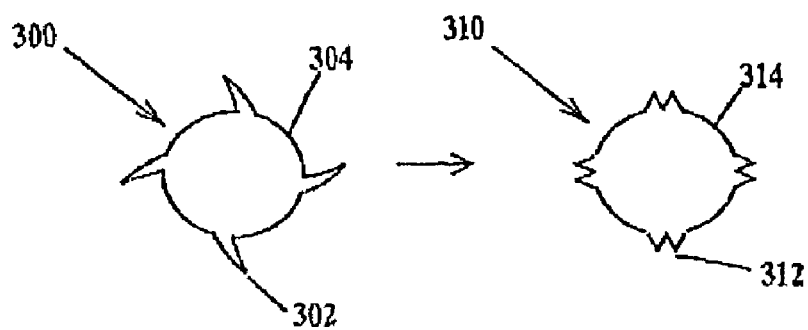
FIG. 13 depicts a cross-section of an alternate expandable sheath of the present invention.
Figure 13:
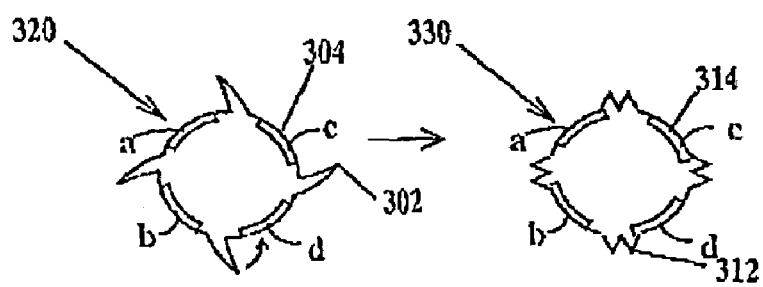
Figure 13:
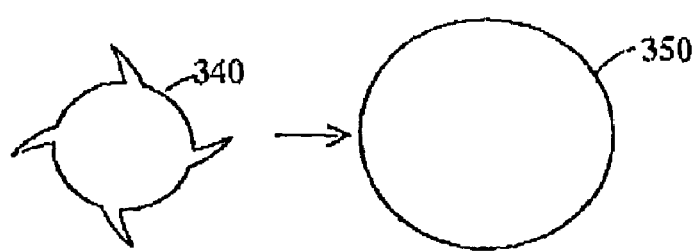

FIG. 13 depicts two alternative embodiments of a semi-rigid stent sheath with predetermined expansion folds. The two embodiments shown each depict a different configuration for the expansion folds. One type of expansion fold embodiment is a flexible hinge fold 300. The fold expansion sites 302 located between semi-rigid sheath sites 304 maintain proper orientation of biodetectors (e.g., microdiodes). In the flexible hinge alternative 302 the flexible region 322 folds flat towards the semi-rigid biodetectors a, b, c, d. The second type of expansion fold embodiment is an accordion fold 310. The fold expansion sites 312 located between semi-rigid sheath sites 314 maintain proper orientation of biodetectors (e.g., microdiodes). The location of the biodetectors a, b, c, d in relation to the accordion folds is shown 330. Flexible circuitry is embedded within the expansion folds of both alternatives. FIG. 13 also depicts the sheath prior to, and after, balloon angioplasty expansion. Prior to expansion 340, a balloon catheter is used to insert the sheath into the body. The balloon catheter then expands the sheath 350.

Figure 14:
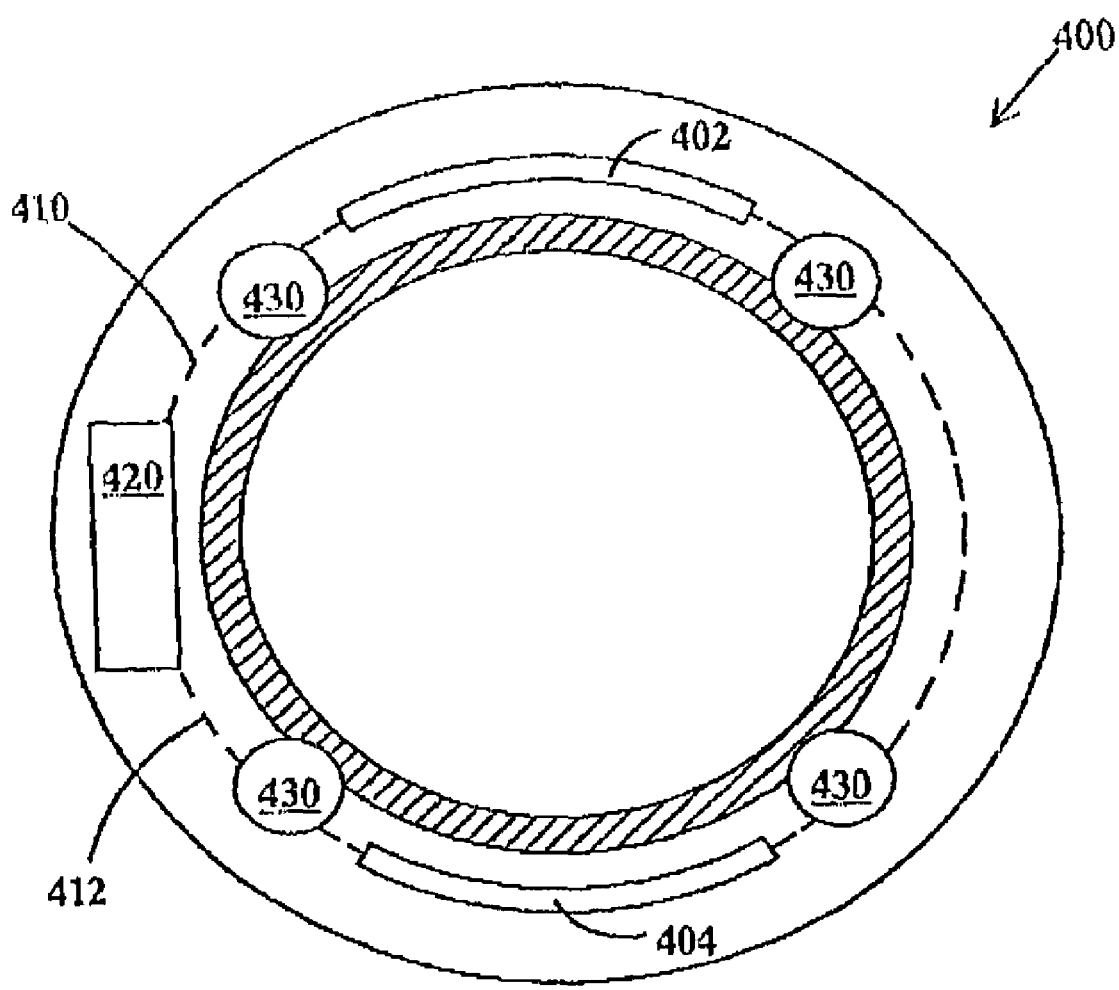
FIG. 14 shows a cross-section of an alternate expandable sheath of the present invention.

FIG. 14 shows a cross-section of a pharmaceutical delivery device. The pharmaceutical delivery device 400. The pharmaceutical delivery device includes biosensors 402, 404 for detecting an occlusive effect or change in diameter Dv. A signal is transmitted through circuit 410, 412 to an integral microchip 420. The circuit may include a nanowire or nanotube or standard circuitry with a biocompatible polymer such as polytetrafluoroethylene or other material as disclosed herein. The microchip 420 calculates the occlusive event and allows pharmaceutical release through microtube 430.

Figure 15A:
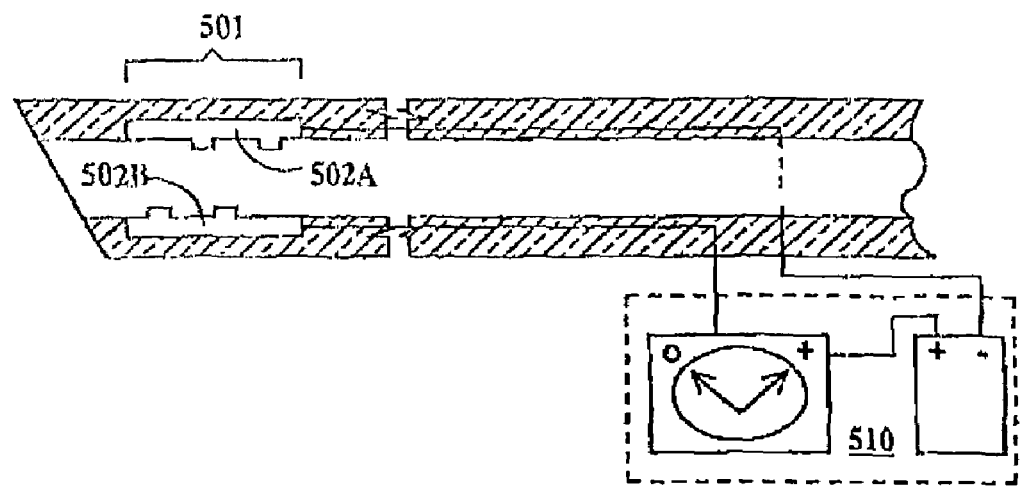
FIG. 15 shows a biodetection catheter.
Figure 15B:
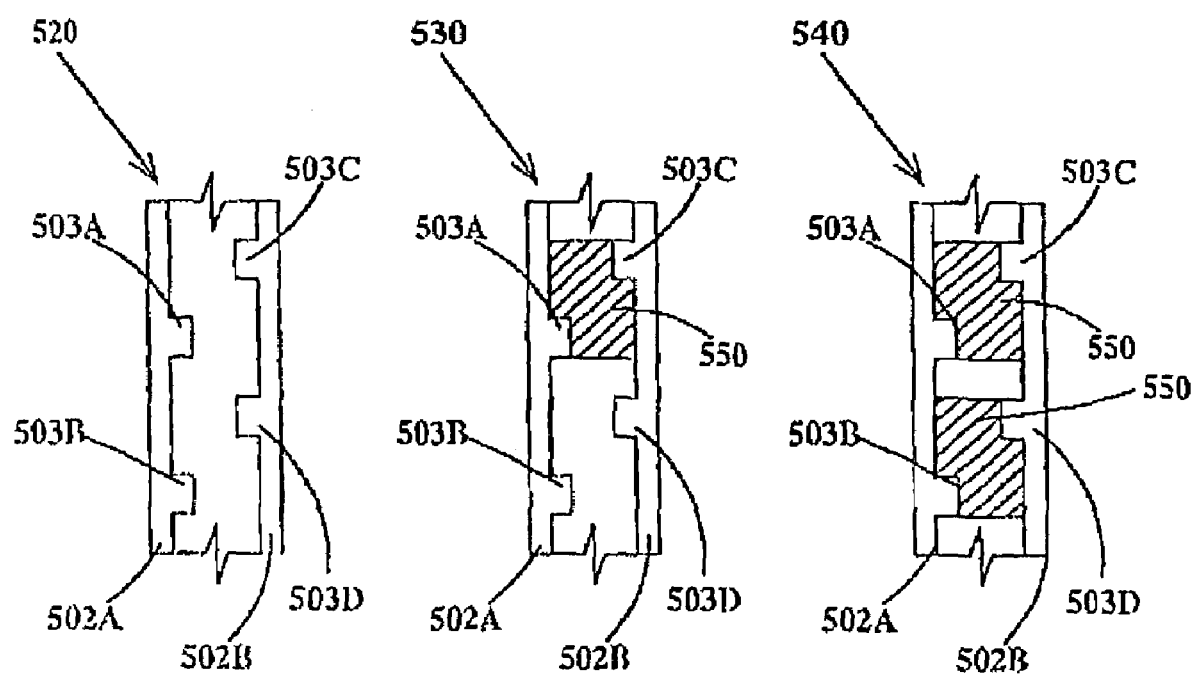

FIG. 15 shows a biodetection catheter 500 having a biodetector 502 embedded in the luminal and external surfaces of the catheter tip. The biodetector 502 includes circuitry as described in the embodiments of FIGS. 1–3, 10 and 14. Alternatively, the microchip and sensor may be external and include an external indicator 510. The biosensor will detect whether a substrate or occlusion is absent 520, present 530 or whether an infection is present 540.

Figure 16:
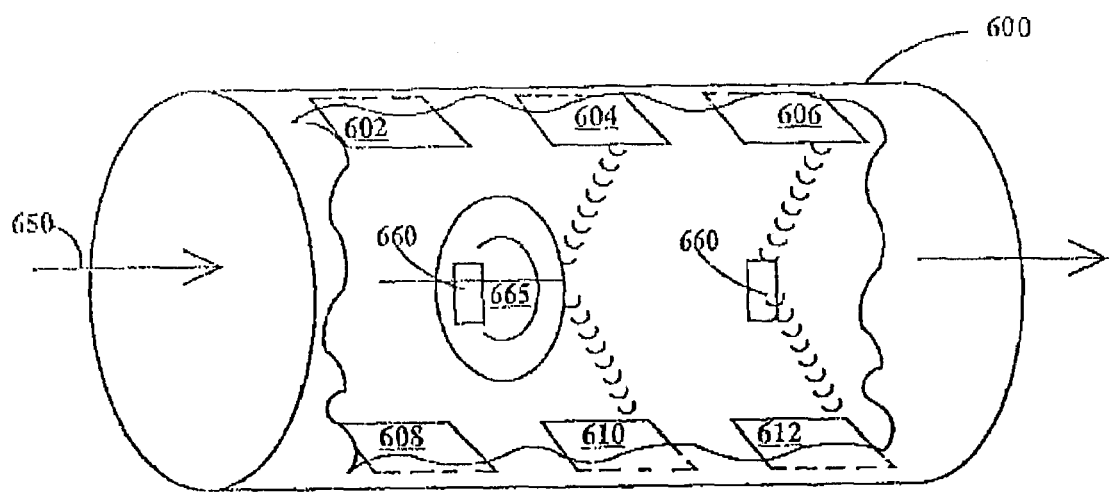
FIG. 16 shows biodetection of nanodevices by a biosensor.
Figure 17:
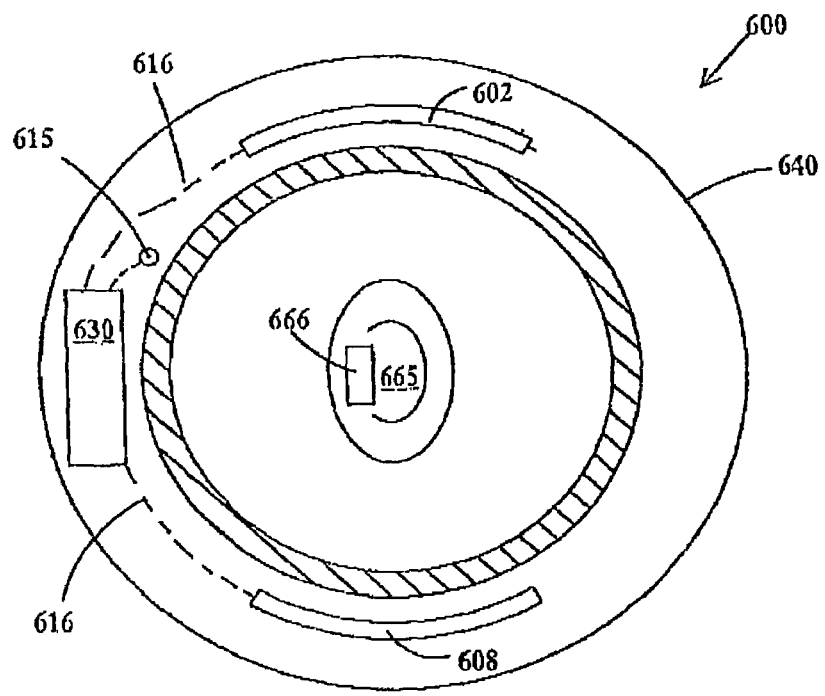
FIG. 17 shows a cross-section of the embodiment of FIG. 16.

FIGS. 16 and 17 disclose biodetection of nanodevices. A stent 600 is shown which includes biosensors 602, 604, 606, 608, 610, and 612. An RF antenna 615 is disclosed. The biosensors transmit data through circuits 616 to a microchip 630. The circuitry is covered by a sheath or biocompatible material 640 as hereinbefore disclosed. Blood flows through the stent in the direction 650. The blood includes nanodevices which are either extracellular 660 or intracellular 666. The intracellular nanodevice is enclosed in a red blood cell 665 through a process such as reverse osmotic lysis or injection.

Figure 18:
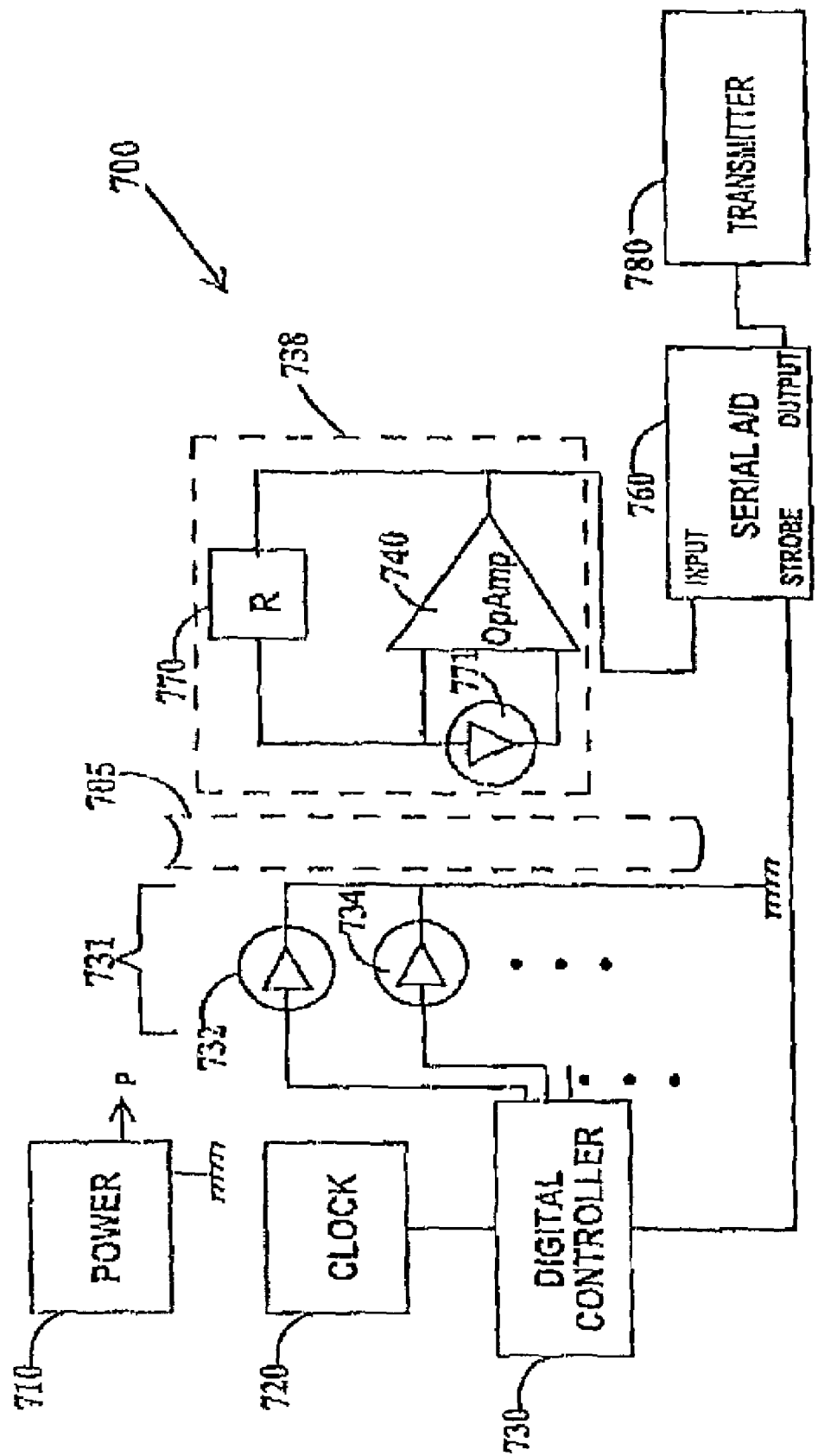
FIG. 18 depicts an instrumented stent oximetry.

FIG. 18 shows instrumented stent oximetry circuitry 700 for biosensing bodily conditions about a stent 705. The circuitry includes a power supply 710, a clock 720, a digital controller 730 which are operatively attached to photodiodes 732, 734 with tranconductance OpAmp 740. The OpAmp 740 and circuit are attached to a serial A/D converter 760 which is attached to a transmitter 780 for conveying an RF signal to an external source.

Figure 19:
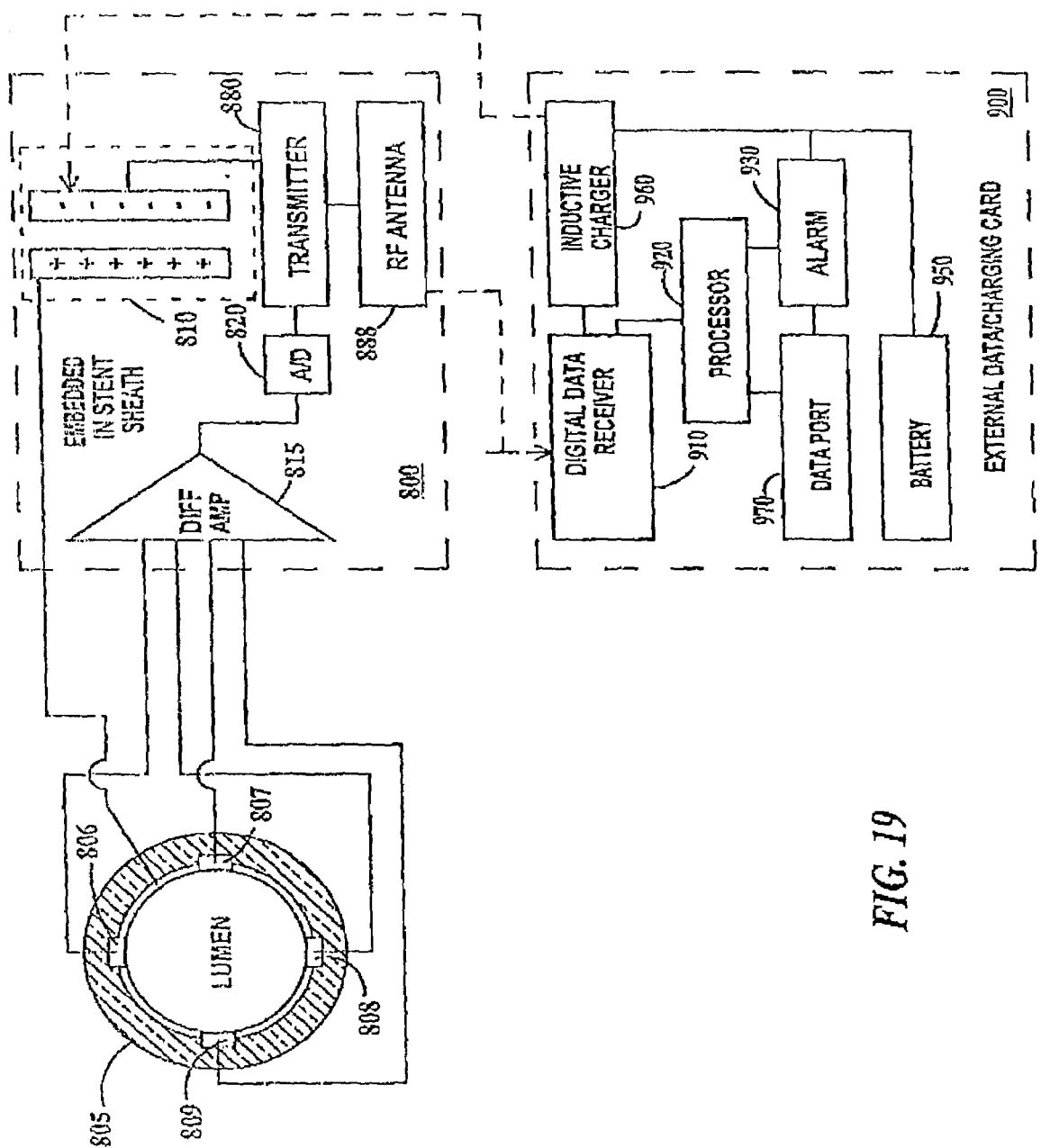
FIG. 19 depicts a biosensor and external receiver and digital processor.

FIG. 19 shows a circuit 800 embedded in a stent 805. The circuit 800 includes an integral capacitor 810 operatively attached to an differential amplifier 815 and an A/D converter. The converter is attached to a transmitter 880 and an RF antenna 888. External to the device is a receiver 900. The receiver 900 may be in the form of a watch, necklace, palm pilot, computer, bracelet or the like. The receiver 900 receives a signal from the circuit 800 through a receiver 910 which processes the information in a processor 920 and provides an output such as an alarm 930. The receiver may also include a battery 950, an inductive charger 960 and a data port 970.

We claim:

1. An apparatus comprising:
    a sheath having an inner and outer surface, wherein the outer surface is adapted for contacting a wall of a body passage, and the inner surface forms a lumen for enabling flow of body fluids therethrough;
    at least two sensors operatively attached to the sheath, for determining changes in a diameter of the lumen, wherein the at least two sensors further are arranged for determining changes due to collapse of the sheath; and
    a means for reporting the changes without an intervening wire.

* * * * *